United States Patent [19]

Kenoff

[11] 4,116,638

[45] Sep. 26, 1978

[54] IMMUNOASSAY DEVICE

[75] Inventor: Michael B. Kenoff, Hackettstown, N.J.

[73] Assignee: Warner-Lambert Company, Morris Plains, N.J.

[21] Appl. No.: 774,190

[22] Filed: Mar. 3, 1977

[51] Int. Cl.² .................................... G01N 33/16
[52] U.S. Cl. ............................... 422/99; 15/304; 424/1; 424/12; 422/104
[58] Field of Search ............... 23/259, 292; 424/12, 424/1; 15/304

[56] References Cited

U.S. PATENT DOCUMENTS

| | | | |
|---|---|---|---|
| 3,464,798 | 9/1969 | Kilthau | 23/292 X |
| 3,492,396 | 1/1970 | Dalton | 424/12 |
| 3,712,465 | 1/1973 | Deuschle | 23/292 X |
| 3,843,444 | 10/1974 | Likhite | 424/12 X |
| 3,849,830 | 11/1974 | Wagner | 15/304 X |
| 3,873,682 | 3/1975 | Ogawa | 424/12 |
| 4,012,200 | 3/1977 | de Leeuw | 23/292 X |

OTHER PUBLICATIONS

Sargent-Welch Catalog, 489, 1971.

Primary Examiner—Sidney Marantz
Attorney, Agent, or Firm—Albert H. Graddis; Frank S. Chow; George M. Yahwak

[57] ABSTRACT

An assembly for use as a solid phase support for immunoassay procedures.

2 Claims, 4 Drawing Figures

IMMUNOASSAY DEVICE

This invention describes a novel device, for use in solid phase immunoassay procedures, which comprises a solid support made of glass or plastic and which is capable of being coated with a specific antigen or antibody.

Prior art devices for solid phase immunoassay procedures now comprise either small beads, vials, or tubes of adsorbant material such as glass and plastics. A difficulty in the techniques using vial or tube devices is that the surface area available for coating with either antigen or antibody is limited to the interior of the device. A difficulty in utilizing small beads of material, as the solid phase support, is that the various wash and "active" solutions are difficult to remove from the reaction vehicle without removing a number of the beads themselves.

An object of the present invention is therefore to disclose a solid support immunoassay device having a large surface area capable of being coated with antigen and antibody.

Another object of the present invention is to disclose a solid support immunoassay device capable of being washed free of reactive and test solutions.

An understanding of the structure and use of the immunoassay device according to this invention may be had by reference to the accompanying drawings in which.

Figure 1:
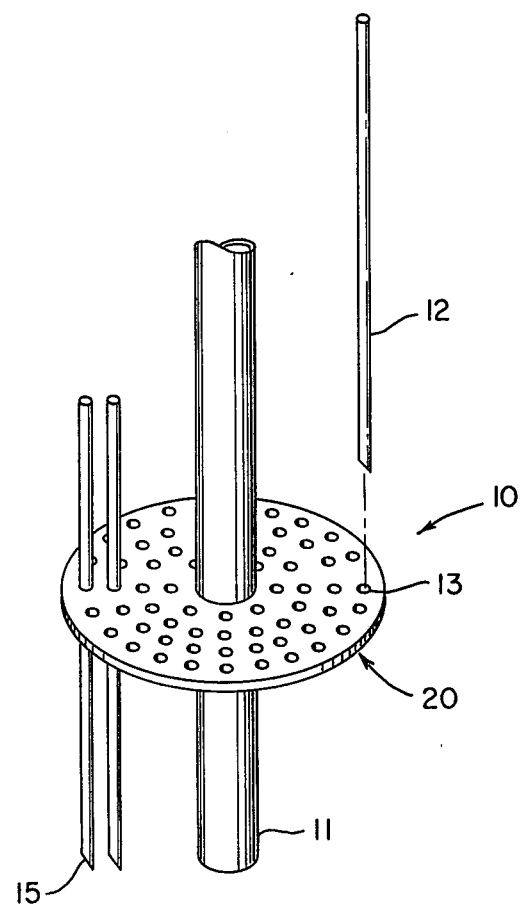
FIG. 1 is a perspective view of the device according to my invention.
Figure 2:
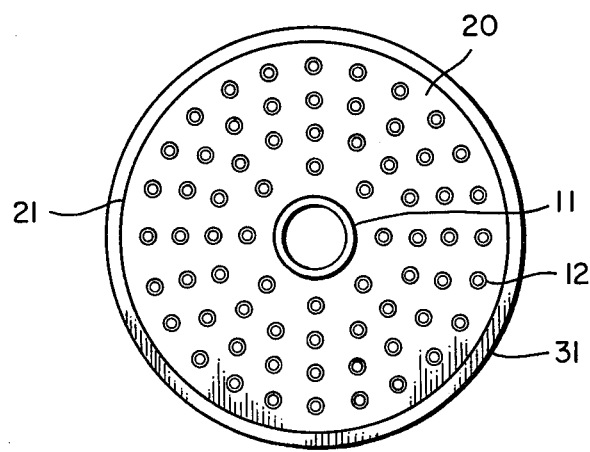
FIG. 2 is a top plan view of the device as seen in FIG. 3.

More particularly, my invention is a novel immunoassay device 10 consisting of a series of capillary tubes 12, such as those conventionally called 5 lambda disposable pipettes, each having a bevel 15 at one end of the tube. A circular disk 20 having a series of radially arranged apertures 13 extending therethrough holds the tubes 12 within the apertures which are of substantially complimentary diameter to the exterior diameter of the tubes 12. Disk 20 further carries a central tubular member 11 of greater length and diameter than the capillary tubes 12.

In use, the device 10 is assembled as indicated at 30 in a vial 31 or as indicated at 40 in a tube 41.

When so assembled, the capillary tubes 12 are aligned so that each point 32 of each bevel 15 just touches the inner surface 33 of the vial or tube to assure maximum capillary uptake. Furthermore, when the device is assembled, disk 20 is of sufficient diameter to abut the interior of vial 31 or tube 41 to hold the device upright and to form a relatively airtight seal 21.

Figure 3:
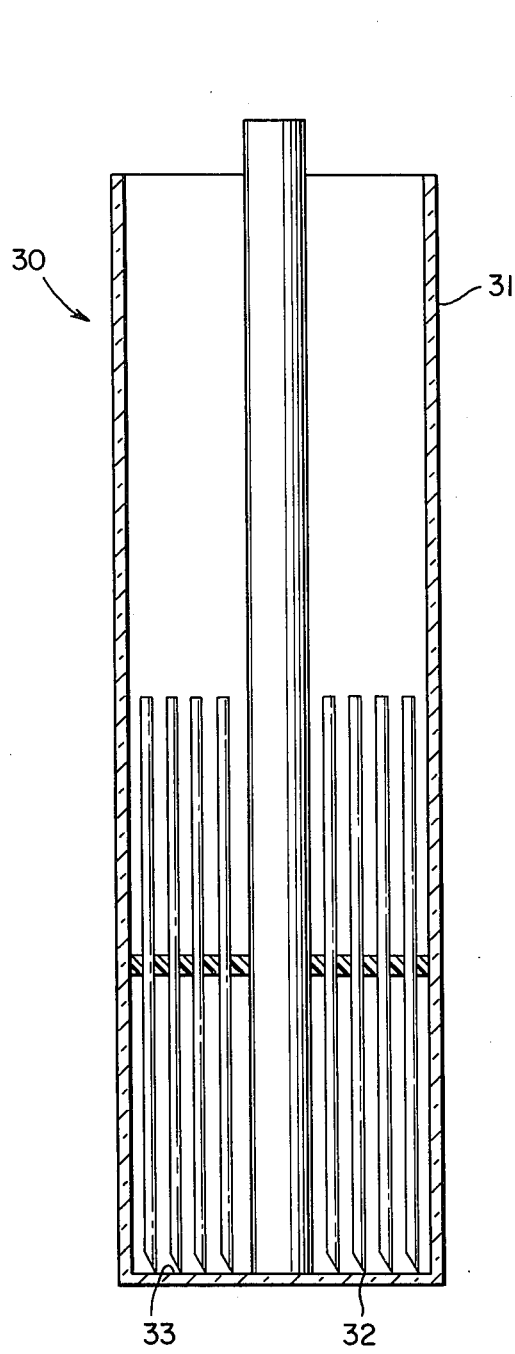
FIG. 3 is a cross-sectional side elevational view of the device according to my invention.
Figure 4:
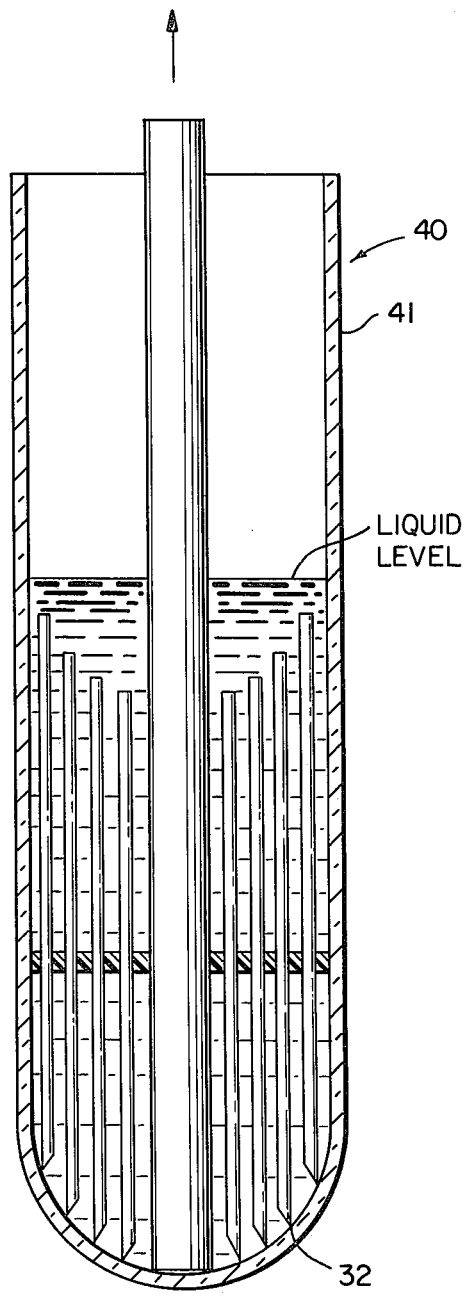
FIG. 4 is a cross-sectional elevational view of the device according to my invention as it appears in use.

As used in this description, vial denotes a flat bottom container as shown in FIG. 3 and tube denotes a round bottom container as shown in FIG. 4. Both the vial and the tube 41 may be optionally sealed as by screw caps if the immunoassay procedure calls for such sealing. The device in either vial 31 or tube 41 can be easily removed to provide a simple method for the introduction of reagents or wash solution. The device can be inserted simply by placing it in an upright position in the vial or tube.

As assembled, the center tube 11 may be used for the introduction or removal of the active and wash solutions conventionally used in immunoassay techniques, as well as serving as means to remove the device from the vial or tube.

A liquid, as shown in FIG. 4, containing a specific antigen is placed into a vial or a tube to a sufficient level to assure that all tubes are exposed to the liquid when the device is inserted into the vial. The antigen, as is known, will bind to the surface of the capillary tubes 12 as well as the disk 20. The antigen containing liquid is then removed after a sufficient coating time has elapsed and the assembly may be washed to remove non adsorbed antigen. Next, the conventional assay procedure will involve the addition of a serum sample containing an unknown quantity of antigen to be measured. Immediately after the addition of the serum containing an unknown quantity of antigen, tagged antibody, either radioactively, fluorescently or enzymatically labeled, specific to the antigen under study is added to the vial or tube and the antigen coated device is immediately inserted into the vial or tube and allowed to form a bound complex with the labeled antibody. The liquid is then removed as indicated by the arrow through the central tube 11. Because of the airtight seal 21 and the bevel portion 15 of the capillary tubes 12 the suction needed to aspirate through the central tube will assure that the interior of each capillary tube 12 will also be aspirated to remove any residual tagged antibody. The assembly is then washed.

As the antibody is radioactively tagged, the device is placed into a radioactive spectrometer and counted; as enzymatically tagged, the enzyme reaction is determined biochemically; if fluorescently tagged, the device is removed and measured in a fluorometer.

Alternatively, if the device is coated with a specific antibody, an unknown serum sample is introduced into the vial and allowed to react with the specific antibody. After a suitable incubation period, the sample is aspirated, the vial is washed and the tagged antibody is introduced into the vial. Tagged antibody is then allowed to react with the antigen bound to the antibody on the solid support. The tagged antibody is removed by aspiration and the assembly is washed as above. The unknown antigen is then quantitated as described above.

Another example for the use of the device coated with a specific antibody is: An unknown sample and tagged antigen are introduced into a vial or tube. Immediately, the antibody coated device is inserted into the vial or tube and allowed to react with the sample and tagged antigen. The binding of tagged antigen to the device is quantitatively exhibited according to the concentration of antigen present in the serum. After a suitable incubation period, the sample is removed, the device washed, and the tagged antigen bound to the support is quantitated as described above.

Having thus described my invention, what is claimed is:

1. A device for carrying out solid phase immunoassays comprising:
    a disk having a plurality of apertures of substantially uniform diameter complimentary to the diameter of the exterior diameter of a capillary tube and said apertures extending through said disc and a center aperture centrally located in said disc and having a greater diameter than the other apertures;

a plurality of capillary tubes of substantially uniform length being maintaind in a spaced relationship to one another by extending through and being held in a number of the plurality of apertures by friction fit; and a tubular member extending through and being frictionally held in the centrally located aperture, said member having a length and a diameter respectively greater than those of said capillary tubes.

2. The device according to claim 1 wherein the capillary tubes have a beveled end portion.

* * * * *